(12) United States Patent
Yao

(10) Patent No.: US 7,872,012 B2
(45) Date of Patent: Jan. 18, 2011

(54) PYRIMIDINONE COMPOUNDS AND PREPARATION AND USE THEREOF

(75) Inventor: Hui Yao, Beijing (CN)

(73) Assignee: Zhejiang Hisun Pharma Co., Ltd., Taizhou Zheijang (CN)

( * ) Notice: Subject to any disclaimer, the term of this patent is extended or adjusted under 35 U.S.C. 154(b) by 831 days.

(21) Appl. No.: 11/722,499

(22) PCT Filed: Dec. 23, 2005

(86) PCT No.: PCT/CN2005/002293

§ 371 (c)(1),
(2), (4) Date: Jul. 30, 2007

(87) PCT Pub. No.: WO2006/066512

PCT Pub. Date: Jun. 29, 2006

(65) Prior Publication Data

US 2008/0280930 A1   Nov. 13, 2008

(30) Foreign Application Priority Data

Dec. 23, 2004   (CN) .................. 2004 1 0101710

(51) Int. Cl.
*C07D 239/36* (2006.01)
*A61K 31/505* (2006.01)
(52) U.S. Cl. ............... 514/274; 544/243; 544/315; 544/318
(58) Field of Classification Search ........... 544/243, 544/315, 318; 514/274
See application file for complete search history.

(56) References Cited

U.S. PATENT DOCUMENTS

| 5,011,930 A | 4/1991 | Fujikawa et al. |
| 5,034,399 A | 7/1991 | Hubsch et al. |
| 5,260,440 A | 11/1993 | Hirai et al. |
| 5,300,477 A | 4/1994 | Tice |

FOREIGN PATENT DOCUMENTS

| DE | 30 45 342 A1 | 7/1982 |
| WO | WO 2004/014872 | 2/2004 |

OTHER PUBLICATIONS

Simone, Oncology: Introduction, Cecil Textbook of Medicine, 20th Edition, vol. 1, pp. 1004-1010, 1996.*
Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition, Revised and Expanded, pp. 451 and 596.*
Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
West, Solid Solutions, Solid State Chemistry and its applications, pp. 358 & 365, 1988.*
Ulrich, Chapter 4: Crystal Characteristics, Kirk Othmer Encyclopedia of Chemical Technology (7 pages), Aug. 2002.*
Vippagunta et al., Crystalline Solids, Advanced Drug Delivery Reviews, 48, pp. 3-26, 2001.*
Danesh et al., Modulatory effects of HMG-CoA reductase inihbitors in diabetic microangiopathy, The FASEB Journal, vol. 18, pp. 805-815, May 2004.*
Vega et al., PubMed Abstract (Circulation 84(1):118-28), 1991.*
Supplementary European Search Report issued in corresponding European Patent Application No. 05824250.4, dated Sep. 9, 2008.
International Search Report for WO 2006/066512 dated Feb. 14, 2006.
Zheng, Hu, *Pharmaceutical Chemistry*, Ed. 4, People's Sanitation Publishing House, Beijing, China, (Dec. 2004) 194-195.

* cited by examiner

*Primary Examiner*—Deepak Rao
(74) *Attorney, Agent, or Firm*—Knobbe, Martens, Olson & Bear, LLP

(57) ABSTRACT

Disclosed are pyrimidinone compounds having formula (I), a preparation and use thereof. The compounds are inhibitors of HMG-CoA reductase, and therefore have antivirus activities and are useful for preventing and treating cardiovascular and cerebrovascular disorders, senile dementia, diabetes mellitus, osteoporosis and tumors, and enhancing immune functions in a subject, and especially useful for treating diseases associated with hyperlipaemia.

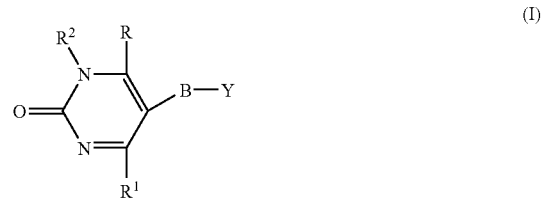

14 Claims, 1 Drawing Sheet

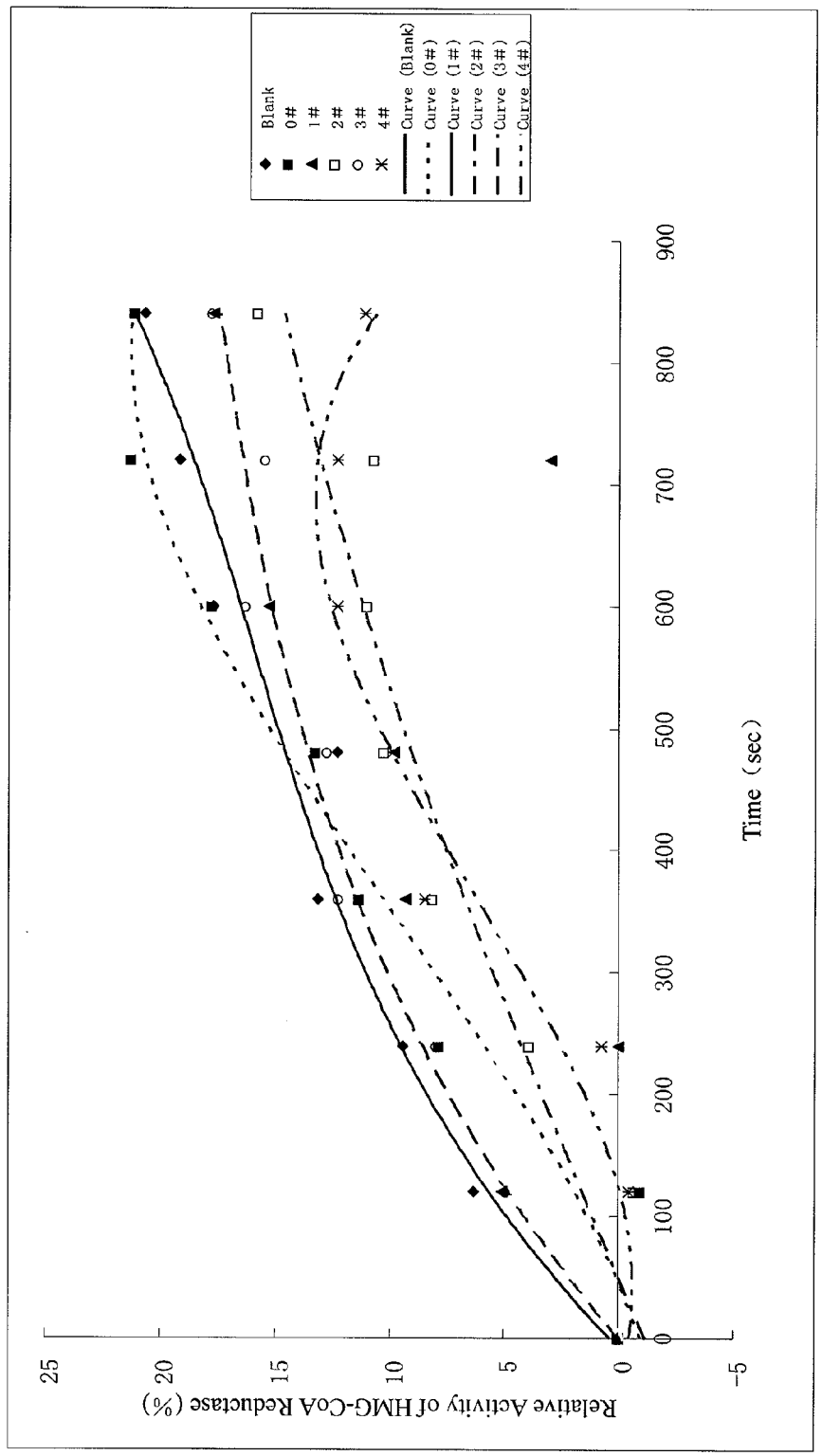
FIG. 1 Relative activity of HMG-CoA reductase at different time (%)
$0^\#$ : Sodium lovastatin ; $1^\#$ : Compound 1a-Na ; $2^\#$ : Compound 1b-Na ; $3^\#$ : Compound 1c-Na ; $4^\#$ : Compound 1d-Na

PYRIMIDINONE COMPOUNDS AND PREPARATION AND USE THEREOF

RELATED APPLICATIONS

This application is the U.S. National Phase filing under 35 U.S.C. §371 of PCT/CN2005/002293, filed Dec. 23, 2005, which designated the United States and was published in a language other than English, which claims priority under 35 U.S.C. §119(a)-(d) to Chinese Patent Application No. 200410101710.X, filed Dec. 23, 2004. The content of these applications is incorporated herein by reference in their entireties.

TECHNICAL FIELDS

The present invention relates to pyrimidinone compounds having antivirus activities and useful for preventing and treating cardiovascular and cerebrovascular disorders, senile dementia, diabetes mellitus, osteoporosis and tumors and enhancing immune functions in subjects, a preparation and use thereof.

TECHNICAL BACKGROUND

It is generally accepted that an elevated serum cholesterol (CH) level (i.e. hyperlipidemia) or, more precisely, an elevated low-density lipoprotein cholesterol (LDL-CH) level, is an important inducement of cerebral apoplexy, coronary heart diseases and myocardial infarction. In addition, hyperlipidemia is also a major risk factor for the development of hypertensive diseases and diabetes mellitus. Hyperlipidemia may further induce hepatic adipose infiltration, hepatic cirrhosis, renal arteriosclerosis, renal failure, gallstone, pancreatitis, subhyaloid hemorrhage, blindness, and cause disorders of male sexual dysfunction, senile dementia, and the like. Recent studies have suggested a potential relationship between hyperlipidemia and onset of some tumors.

The discovery of statins, one of HMG-CoA (3-hydroxy-3-methylglutaryl coenzyme A) reductase inhibitors, in 1970s broke a new path for the development of antihyperlipidemic drugs. Statins have a common active dihydroxy-heptanoic acid moiety that can be hydrolyzed in vivo into a β-hydroxy acid. As the β-hydroxy acid has a chemical structure similar to HMG-CoA, it can competitively bind to HMG-CoA reductase that catalyzes the conversion of HMG-CoA to mevalortic acid, thereby reducing the activity of the reductase, blocking the cholesterol biosynthesis, and promoting the increment of the amount and activity of LDL receptors on the surface of liver cells. Thus, the reduction of a serum LDL cholesterol level is promoted and thus the total serum cholesterol level is reduced so that diseases associated with hyperlipidemia can be treated.

Recent studies have shown that statins possess lots of properties besides adjusting serum cholesterol. The studies of American Cancer Society have shown that statins have activities for preventing and treating acute myeloblastic leukemia, colon carcinoma, breast carcinoma, and carcinoma of head of pancreas. The study of CARE demonstrates that pravastatin can cut down the risk of colon carcinoma by 43%, and the study of 4S demonstrates that simvastatin can cut down the risk of colon carcinoma by 19%. Simvastatin shows a lethal effect to myeloid progenitor cells of both normal people and patients suffering from acute myeloblastic leukemia, and can be used as an ancillary drug in chemotherapy. In a report of Doctor Banke Agarwal of St. Luke's-Roosevelt Hospital center, Colombia University, New York, it is suggested that statins and non steroidal anti-inflammatory drugs (NSAIDs) have synergetic effects on preventing colorectal cancer.

Statins can also be used to treat osteoporosis. Clinical trials on human prove that statins have sclerotin reparation effects at a dosage proposed for treating hyperlipidemia. The mechanism of the effect of statins on osteoporosis lies in the competitive inhibition of HMG CoA reductase, thereby reducing the biosynthesis of cholesterol in liver and its direct metabolite, mevalonate. Meanwhile, researchers have found that mevalonate may have an activity for inhibiting the promoter of bone morphogenetic protein-2 (BMP-2) gene, and this answers why statins have biological effects on bones.

Studies have demonstrated that a long term administration of statins can reduce the risk of cerebral apoplexy by 11-31%. And the study in Loyola University Medical Center, Chicago, Ill. U.S.A, shows that the morbidity of Alzheimer disease in patients taking lovastatin (Mevacor) and pravastatin (Pratchd) is 60-73% lower than those taking other medicaments for treating cardiovascular and cerebrovascular disorders or hypertensive diseases.

Furthermore, the most recent studies have shown that statins have protecting effects on kidney that are independent of their anti-hyperlipidemia properties. The serum concentration of C-active protein (CRP) is lowered in patients taking statins, which demonstrates that a long term administration of statins can cut down the risk of cardiovascular and cerebrovascular disorders by abating inflammations.

There have been a number of references in the art relating to statins compounds and preparation thereof. For example, U.S. Pat. No. 5,034,399 discloses substituted 1,8-naphthyridines as inhibitors of HMG-CoA reductase, their preparation and their use in medicaments.

U.S. Pat. No. 5,011,930 discloses mevalonolactones having a quinoline ring as inhibitors of HMG-CoA reductase, processes for their production and their pharmaceutical uses. All references mentioned above are explicitly incorporated herein by reference in their entirety.

SUMMARY OF THE INVENTION

In a first aspect, the present invention relates to a compound of formula (I),

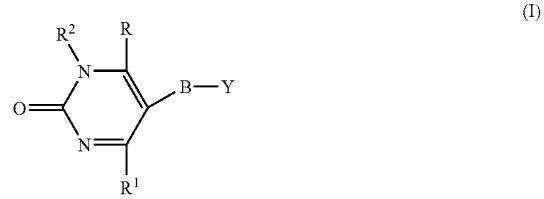

in which

R and $R^1$ are independently selected from the group consisting of hydrogen, alkyl, cycloalkyl, alkenyl, cycloalkenyl, aryl and heteroaryl groups, which (except hydrogen) may be substituted by 1 to 3 substituents selected from the group consisting of halogen, $R^3R^4N\text{---}$, $NO_2$ CN, OH, alkyl, alkoxy, haloalkyl, aryloxy, aralkoxy, acyl, sulfonyl and sulfinyl, where each $R^3$ and $R^4$ independently represents H, alkyl or aryl;

$R^2$ is selected from the group consisting of hydrogen, alkyl, cycloalkyl, alkenyl, cycloalkenyl, aryl and heteroaryl groups, which (except hydrogen) may be substituted by 1 to 3 substituents selected from the group consisting of halogen, $R^3R^4N—$, $NO_2$ CN, OH, alkyl, cycloalkyl, aryl, alkoxy, aryloxy, aralkoxy, alkylthio, arylthio, aralkylthio, acyl, sulfonyl and sulfinyl, where $R^3$ and $R^4$ are as defined previously;

B is $—CH_2—CH_2—$ or $—CH=CH—$; and

Y represents

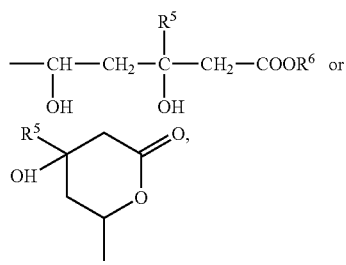

where $R^5$ is hydrogen or alkyl, and $R^6$ represents hydrogen, alkyl, alkenyl, aryl, aralkyl, alkaryl or a pharmacologically non-toxic ion, a pharmaceutically acceptable solvate and a physiologically functional derivative thereof.

In a second aspect, the present invention relates to a pharmaceutical composition comprising an effective amount of a compound of formula (I), a pharmaceutically acceptable solvate or a physiologically functional derivative thereof, and a pharmaceutically acceptable carrier.

In a third aspect, the present invention relates to use of a compound of formula (I) in manufacturing an antiviral medicament, a medicament for preventing or treating cardiovascular and cerebrovascular disorders, senile dementia, diabetes mellitus, osteoporosis or tumors, or a medicament for enhancing immune functions in a subject.

In a fourth aspect, the present invention relates to a method for preventing or treating cardiovascular and cerebrovascular disorders, senile dementia, diabetes mellitus, osteoporosis or tumors in a subject, which comprises administering to the subject a therapeutically effective amount of a compound of formula (I), a pharmaceutically acceptable solvate or a physiologically functional derivative thereof.

In some preferred embodiments of the invention, the prevention and treatment of the above-mentioned diseases are benefited from the inhibition of HMG-CoA reductase.

In a fifth aspect, the present invention relates to a process for the preparation of a compound of formula (I), which comprises:

a) reacting a compound of formula (II),

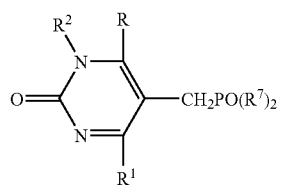

(II)

in which R, $R^1$ and $R^2$ are as defined previously, and $R^7$ represents alkyl, alkoxy, aryl or $R^3R^4N—$, where $R^3$ and $R^4$ are as defined previously, with a compound of formula (III),

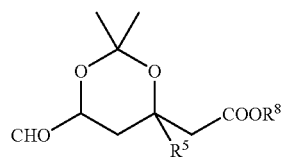

in which $R^5$ is as defined previously and $R^8$ is alkyl or aryl, so as to obtain a compound of formula (IV)

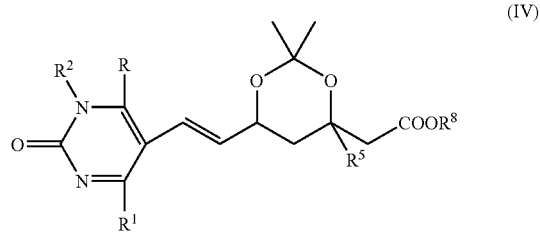

(IV)

in which R, $R^1$, $R^2$, $R^5$ and $R^8$ are as defined previously; and b) converting the compound of formula (IV) into the compound of formula (I).

In a sixth aspect, the present invention relates to the intermediate of formula (II),

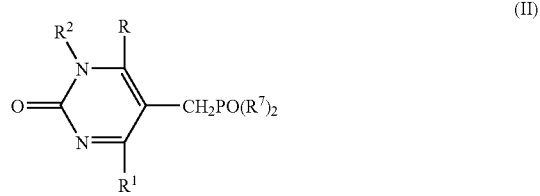

(II)

in which R, $R^1$, $R^2$ and $R^7$ are as defined previously.

BRIEF DESCRIPTION OF DRAWINGS

FIG. 1 is a plot showing the effects of compounds of the invention and sodium lovastatin versus time at a dose of 100 mg/L on the inhibition of HMG-CoA reductase.

DETAILED DESCRIPTION OF THE INVENTION

Hereinafter, some preferred embodiments of the present invention will be described in details for a better understanding thereof. It should be appreciated that the embodiments are furnished only for a purpose of illustration and do not constitute any limitations to the invention.

The term "physiologically functional derivative(s)", as used herein, refers to a derivative of a pharmacologically active compound, which per se has no pharmacological activities but can be converted into the active compound in vivo upon administration.

The term "pharmaceutically acceptable solvate(s)" used herein means a hydrate or a solvate comprising other pharmaceutically acceptable solvents of crystallization such as alcohols.

The term "alkyl" used herein generally refers to a linear or branched saturated aliphatic group, preferably $C_1$-$C_8$ alkyl, and more preferably $C_1$-$C_6$ alkyl, including but not limited to methyl, ethyl, n-propyl, iso-propyl, n-butyl, iso-butyl, 1-methylpropyl, tert-butyl, n-pentyl, iso-pentyl, 1-methylbutyl, tert-pentyl, n-hexyl, iso-hexyl, 1-methylpentyl, 1,1-dimethylbutyl, 1,2-dimethylbutyl, 1,1-diethylethyl, tert-hexyl, and the like.

The term "alkenyl" used herein generally refers to a linear or branched unsaturated aliphatic group having one or more C=C double bonds, preferably $C_2$-$C_8$ alkenyl, and more preferably $C_2$-$C_6$ alkenyl, including but not limited to ethenyl, propenyl, 2-propenyl, butenyl, 2-butenyl, 3-butenyl, iso-butenyl, pentenyl, 2-pentenyl, 3-pentenyl, iso-pentenyl, and the like.

The term "cycloalkyl" used herein generally refers to a saturated alicyclic group, preferably $C_3$-$C_8$ cycloalkyl, and more preferably $C_3$-$C_6$ cycloalkyl, such as cyclopropyl, cyclobutyl, cyclopentyl and cyclohexyl.

The term "cycloalkenyl" used herein generally refers to an unsaturated alicyclic group having one or more C=C double bonds, preferably $C_3$-$C_8$ cycloalkenyl, and more preferably $C_3$-$C_6$ cycloalkenyl, such as cyclopropenyl, cyclobutenyl, cyclopentenyl and cyclopentadienyl.

The term "aryl" used herein generally refers to a carbocyclic aromatic group, including fused aromatic groups. Preferably, the aryl is $C_6$-$C_{20}$ aryl, more preferably is $C_6$-$C_{12}$ aryl such as phenyl, xenyl, naphthyl and the like, and even more preferably is phenyl.

The term "heteroaryl" used herein generally refers to an aromatic group including fused groups, in which one or more ring carbon atoms are replaced by one or more hetero-atoms selected form the group consisting of N, O, P and S. Preferred heteroaryl is a heteroaryl group having 5-11 carbon atoms, including but not limited to pyridyl, thienyl, furyl, imidazolyl and the like.

The term "acyl" used herein involves alkanoyl and aroyl groups, such as formyl, acetyl, propionyl, butyryl, isobutyryl, benzoyl and the like.

The term "sulfonyl" used herein involves sulfonyl groups substituted with alkyl, aryl or amino, such as mesyl, phenylsulfonyl, mesylamino, dimethylsulfonylamino and the like.

The term "pharmacologically non-toxic ion(s)" used herein involves ions of alkali metals, alkaline-earth metals, ammonium and the like, such as lithium, sodium, potassium, calcium, magnesium and cesium etc.

The term "halogen" used herein involves fluorine, chlorine, bromine, iodine, and preferably fluorine and chlorine.

An aspect of the present invention is directed to a compound of formula (I),

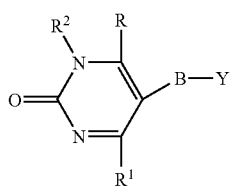

(I)

in which

R and $R^1$ are independently selected from the group consisting of hydrogen, alkyl, cycloalkyl, alkenyl, cycloalkenyl, aryl and heteroaryl groups, which (except hydrogen) may be substituted by 1 to 3 substituents selected from the group consisting of halogen, $R^3R^4N-$, $NO_2$, CN, OH, alkyl, alkoxy, haloalkyl, aryloxy, aralkoxy, acyl, sulfonyl and sulfinyl, where each $R^3$ and $R^4$ independently represents H, alkyl or aryl;

$R^2$ is selected from the group consisting of hydrogen, alkyl, cycloalkyl, alkenyl, cycloalkenyl, aryl and heteroaryl groups, which (except hydrogen) may be substituted by 1 to 3 substituents selected from the group consisting of halogen, $R^3R^4N-$, $NO_2$, CN, OH, alkyl, cycloalkyl, aryl, alkoxy, aryloxy, aralkoxy, alkylthio, arylthio, aralkylthio, acyl, sulfonyl and sulfinyl, where $R^3$ and $R^4$ are as defined previously;

B is $-CH_2-CH_2-$ or $-CH=CH-$; and

Y represents

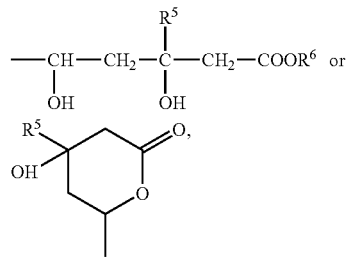

where $R^5$ is hydrogen or alkyl, and $R^6$ represents hydrogen, alkyl, alkenyl, aryl, aralkyl, alkaryl or a pharmacologically non-toxic ion, a pharmaceutically acceptable solvate and a physiologically functional derivative thereof.

According to a preferred embodiment of the invention, R and $R^1$ are independently selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $NO_2$, CN, OH, $C_1$-$C_6$ alkyl, $C_1$-$C_6$ haloalkyl, $C_1$-$C_6$ alkoxy, $C_6$-$C_{12}$ aryloxy, $C_7$-$C_{20}$ aralkoxy and $C_1$-$C_6$ alkanoyl.

According to a further preferred embodiment of the invention, R and $R^1$ are independently selected from the group consisting of hydrogen, $C_1$-$C_6$ alkyl, and $C_6$-$C_{12}$ aryl groups, which (except hydrogen) may be substituted by 1 to 3 substituents selected from the group consisting of F, Cl, $NO_2$, CN, OH, $C_1$-$C_6$ alkyl, $C_1$-$C_6$ haloalkyl, and $C_1$-$C_6$ alkoxy.

According to another preferred embodiment of the invention, $R^2$ is selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $NO_2$, CN, OH, $C_1$-$C_6$ alkyl, $C_3$-$C_8$ cycloalkyl, $C_6$-$C_{12}$ aryl, $C_1$-$C_6$ alkoxy, $C_6$-$C_{12}$ aryloxy, $C_7$-$C_{20}$ aralkoxy, $C_1$-$C_6$ alkylthio, $C_6$-$C_{12}$ arylthio, $C_7$-$C_{20}$ aralkylthio, and $C_1$-$C_6$ alkanoyl.

According to a further preferred embodiment of the invention, $R^2$ is selected from the group consisting of hydrogen, $C_1$-$C_6$ alkyl, $C_3$-$C_8$ cycloalkyl, and $C_6$-$C_{12}$ aryl groups, which (except hydrogen) may be substituted by 1 to 3 substituents selected from the group consisting of F, Cl, $NO_2$, CN, OH, $C_1$-$C_6$ alkyl, $C_3$-$C_8$ cycloalkyl, $C_6$-$C_{12}$ aryl, $C_1$-$C_6$ alkoxy, $C_6$-$C_{12}$ aryloxy, $C_7$-$C_{14}$ aralkoxy, $C_1$-$C_6$ alkylthio, and $C_6$-$C_{12}$ arylthio.

According to another preferred embodiment of the invention, $R^5$ is hydrogen or $C_1$-$C_6$ alkyl, According to other preferred embodiments of the invention, $R^6$ represents hydrogen, $C_1$-$C_6$ alkyl, $C_2$-$C_6$ alkenyl, $C_6$-$C_{12}$ aryl, $C_7$-$C_{20}$ aralkyl, $C_7$-$C_{20}$ alkaryl or a pharmacologically non-toxic ion. More preferably, $R^6$ represents hydrogen, $C_1$-$C_6$ alkyl, $C_6$-$C_{12}$ aryl, or sodium, potassium, calcium or magnesium ions.

According to a still further preferred embodiment of the invention, R and $R^1$ are independently selected from the group consisting of $C_1$-$C_6$ alkyl and $C_6$-$C_{12}$ aryl groups, which may be substituted by 1 to 3 substituents selected from the group consisting of F, Cl, $NO_2$, CN and $C_1$-$C_6$ alkyl; $R^2$ is selected from the group consisting of hydrogen, $C_1$-$C_6$ alkyl, $C_3$-$C_6$ cycloalkyl, and $C_6$-$C_{12}$ aryl groups, which (except hydrogen) may be substituted by 1 to 3 substituents selected from the group consisting of OH, $C_1$-$C_6$ alkyl, $C_3$-$C_6$ cycloalkyl, $C_6$-$C_{12}$ aryl, $C_1$-$C_6$ alkoxy, $C_6$-$C_{12}$ aryloxy, and $C_7$-$C_{14}$ aralkoxy; $R^5$ is hydrogen or $C_1$-$C_6$ alkyl; and $R^6$ represents hydrogen, $C_1$-$C_6$ alkyl, or Na, K, or Ca ions.

The compounds of formula (I) according to the present invention have several asymmetric carbon atoms, thereby existing in various stereochemical forms. The present invention thus involves all individual stereo-isomers of the compounds of formula (I) and mixtures thereof.

The individual stereo-isomers can be obtained by direct asymmetric synthesis using optically pure reactants, or by resolution of racemates. The resolution of racemates can be performed using conventional methods well-known in the art, such as the method as described in U.S. Pat. No. 5,034,399.

According to a preferred embodiment of the invention, B is (E)-CH=CH—.

According to another preferred embodiment of the invention, the two hydroxyl groups on the Y chain are present in a (3R,5S) configuration.

According to a particularly preferred embodiment of the invention, the compound of formula (I) is selected from:

tert-butyl (E)-7-[4'-(4"-fluorophenyl)-6'-isopropyl-2'-oxo-3'-methyl-pyrimidin-5'-yl]-(3R,5S)dihydroxyl-hept-6-enoate;

sodium (E)-7-[4'-(4"-fluorophenyl)-6'-isopropyl-2'-oxo-3'-methyl-pyrimidin-5'-yl]-(3R,5S)dihydroxyl-hept-6-enoate;

sodium (E)-7-[4'-(4"-fluorophenyl)-6'-isopropyl-2'-oxo-pyrimidin-5'-yl]-(3R,5S) dihydroxyl-hept-6-enoate;

sodium (E)-7-[4'-(4"-methylphenyl)-6'-isopropyl-2'-oxo-3'-benzyl-pyrimidin-5'-yl]-(3R,5S)dihydroxyl-hept-6-enoate;

sodium (E)-7-[4'-(4"-fluorophenyl)-6'-isopropyl-2'-oxo-3'-(benzyloxymethyl)-pyrimidin-5'-yl]-(3R,5S)dihydroxyl-hept-6-enoate;

tert-butyl (E)-7-[4'-(4"-fluorophenyl)-6'-isopropyl-2'-oxo-3'-(ethoxylmethyl)-pyrimidin-5'-yl]-(3R,5S)dihydroxyl-hept-6-enoate;

tert-butyl (E)-7-[4'-(4"-fluorophenyl)-6'-isopropyl-2'-oxo-3'-(2"-ethoxylethyl)-pyrimidin-5'-yl]-(3R,5S)dihydroxyl-hept-6-enoate;

tert-butyl (E)-7-[4'-(4"-fluorophenyl)-6'-isopropyl-2'-oxo-3'-cyclopropyl-pyrimidin-5'-yl]-(3R,5S)dihydroxyl-hept-6-enoate; and tert-butyl (E)-7-[4'-(4"-fluorophenyl)-6'-isopropyl-2'-oxo-3'-cyclopropylmethyl-pyrimidin-5'-yl]-(3R,5S)dihydroxyl-hept-6-enoate.

Another aspect of the invention is directed to a pharmaceutical composition comprising an effective amount of a compound of formula (I), a pharmaceutically acceptable solvate or a physiologically functional derivative thereof, and a pharmaceutically acceptable carrier.

Carriers may be used in the present invention include pharmaceutically acceptable organic or inorganic carriers suitable for parenteral and intestinal (oral) administration, which have no adverse effects on the active ingredient. Suitable pharmaceutically acceptable carriers include, but are not limited to, water, saline solution, alcohols, acacia, vegetable oils, benzalcohol, polyethylene glycol, gelatin, sugars (such as lactose), amylose or starch, magnesium stearate, talc, silicic acid, viscous paraffin, volatile oil, fatty acid monoglycerides and diglycerides, pentaerythritol fatty acid ester, carboxymethyl cellulose, polyvinylpyrrolidone, hydroxypropyl methyl cellulose, cellulose acetate phthalate, acrylic resin, hypromellose phthalate and analogous compounds.

The concentration of the active compound in the composition according to the present invention may vary depending on its absorption, distribution, metabolism and evacuating rate in vivo, as well as other factors well known in the art. It will be appreciated that the dose of the composition may vary according to the severity of conditions to be treated, and the dosage schemes for a specific subject may be adjusted with the process of time according to the judgments of a professional.

The composition of the invention can be formulated into various pharmaceutically acceptable dosage forms, in which a suitable pharmaceutically acceptable carrier may be used. Such dosage forms include, but are not limited to capsules (including sustained-release or delayed-release dosage forms), tablets, powders, solutions, suspensions, syrups, pills, granules, elixirs, tinctures, implants (including suppository), emulsions, and injections, preferably gastro-resistant capsules or tablets.

For parenteral administration, the suitable dosage forms include injectable sterile solutions, lyophilized formulations, suspensions, emulsions and the like.

For intestinal administration, the suitable dosage forms include tablets, dragees, liquor, drops and capsules. By using a sweet excipient, the composition of the invention can be formulated into forms of syrups, tinctures and the like.

In some embodiments, the preparations of the invention may be administered alone or in combination with other active agents, such as nicotinic acid.

Still another aspect of the present invention is directed to use of a compound of formula (I) in manufacturing an antiviral medicament, a medicament for preventing or treating cardiovascular and cerebrovascular disorders, senile dementia, diabetes mellitus, osteoporosis or tumors, or a medicament for enhancing immune functions in subjects.

According to some preferred embodiments of the invention, the medicaments take effects by inhibiting HMG-CoA reductase.

Still another aspect of the present invention is directed to a method for preventing or treating cardiovascular and cerebrovascular disorders, senile dementia, diabetes mellitus, osteoporosis or tumors in a subject, which comprises administering to the subject an therapeutically effective amount of a compound of formula (I), a pharmaceutically acceptable solvate or a physiologically functional derivative thereof.

According to some preferred embodiments of the invention, the prevention and treatment of the above-mentioned diseases may be benefited from the inhibition of HMG-CoA reductase.

For treatment of any disease mentioned above, the compound of formula (I), a pharmaceutically acceptable solvate or a physiologically functional derivative thereof may be administered, for example, orally or parenterally at an effective amount in a suitable formulation (optionally including various conventional pharmaceutically acceptable carriers). Furthermore, the active ingredient may be administered alone or in combination with other active agents such as nicotinic acid, in a single dose or in multiple smaller doses at various intervals.

Solid dosage forms for oral administration include tablets, pills, granules, capsules, and the like. The solid dosage forms may comprise any of the following components or any compound having similar properties: excipients such as microcrystalline cellulose, sodium citrate, calcium carbonate, dipotassium phosphate and glycine; disintegrants (dispersants) such as starch more preferably corn, potato or tapioca starch, alginic acid, sodium carbonate and certain complex silicates; binders like polyvinylpyrrolidone, sucrose, gelatin and acacia; humectants such as, for example, glycerol; solution retarding agents, such as, for example paraffin; absorption accelerators such as, for example, quartenary ammonium compounds; wetting agents like cetyl alcohol and glycerol monostearate; absorbents like kaolin, bentonite and clay; and flavorings such as peppermint, methyl salicylate, and orange flavoring. Additionally, magnesium stearate, sodium lauryl sulfate, talc, calcium stearate, solid polyethylene glycols and mixtures thereof are often added as lubricating agents for tabletting purposes. Besides the components mentioned above, liquid carriers such as fatty acids can also be used in capsules. The solid dosage forms of tablets, capsules, pills, and the granules can be prepared with coatings and shells such as enteric coatings, release controlling coatings and other coatings that are well known in the field of pharmaceutical formulation art. In the case of capsules, tablets and pills, the dosage form may also comprise buffering agents. They may also be so formulated that they release the active ingredient(s) only or preferentially in a certain part of the intestinal tract, optionally in a delayed manner. The active compounds can also be in micro-encapsulated form using one or more of the excipients noted above.

Liquid dosage forms for oral administration include emulsions, microemulsions, solutions, suspensions, syrups, and the like. The diluents may be selected from the group consisting of water, ethanol, propylene glycol, isopropyl alcohol, ethyl carbonate, ethyl acetate, benzyl alcohol, benzyl benzoate, 1,3-butylene glycol, dimethyl formamide, oils such as cottonseed, groundnut, corn, germ, olive, castor, sesame oils and the like, glycerol, tetrahydrofurfuryl alcohol, polyethylene glycols and esters of fatty acids like sorbitan and various combination thereof. For such oral consumption it is desirable to combine the active ingredient with various sweetening or flavoring agents, coloring matter or dyes, if so desired.

The dosage forms for parenteral administration, such as solutions and suspensions, may contain any of the following components: sterile diluents such as water for injection, saline, fixed oil, polyethylene glycol, glycerol, propanediol and other synthesized solvents; antioxidants such as ascorbic acid and sodium bisulfite; complexants such as EDTA; buffering agents such as acetates, citrate and phosphate; and tension adjusting agents such as sodium chloride and glucose. The preparation can be loaded into glass or plastic ampoules, disposable syringes or multi-dose vials. For intravenous administration, preferred carriers include saline, PBS, and auxiliaries including, but not limited to, alum, aluminium phosphate and other oil- or water-emulsion auxiliaries.

Suitable doses of the compound according to the present invention for human may vary depending on the body weight and gender of the subject in need of such treatment, the disease to be treated and its condition, and the route of administration, and would be readily determined by those skilled in the art.

Still another aspect of the present invention is directed to a process for the preparation of a compound of formula (I), which comprises:

b) reacting a compound of formula (II),

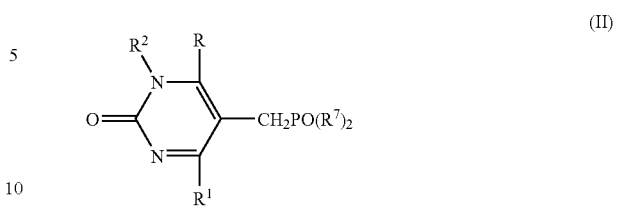

in which R, $R^1$ and $R^2$ are as defined previously, and $R^7$ represents alkyl, alkoxy, aryl or $R^3R^4N$—, where $R^3$ and $R^4$ are as defined previously, with a compound of formula (III),

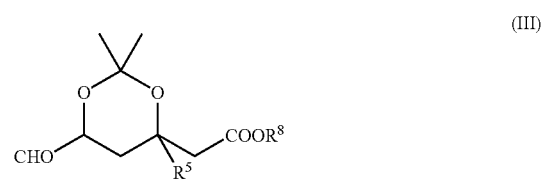

in which $R^5$ is as defined previously and $R^8$ is alkyl or aryl, so as to obtain a compound of formula (IV)

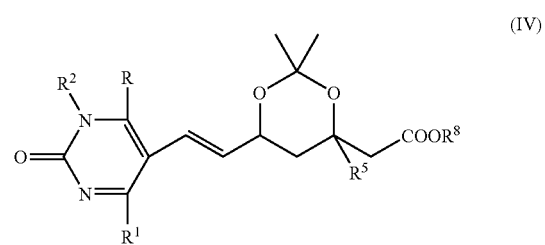

in which R, $R^1$, $R^2$, $R^5$ and $R^8$ are as defined previously; and b) converting the compound of formula (IV) into the compound of formula (I).

The compound of formula (II) is a novel intermediate, and the compound of formula (III) can be prepared according to the method as described in K. Takahashi et al., *Bull. Chem. Soc. Jpn.*, 1995, 68, 364-372.

Preferably, step a) is carried out at the presence of a base including metal hydroxides, alkyl lithium, carbonates, acetates, organic amino lithium and the like, such as NaH, LiH, $CaH_2$, LiBu-n, LiCl, $Li_2CO_3$, $Na_2CO_3$, NaOAc and triethylamine. More preferably, the base is selected from the group consisting of LiBu-n and organic amino lithium.

Preferably, step a) is carried out in an anhydrous inert organic solvent, at a temperature ranging from −78° C. to the reflux temperature of the solvent, for 30 minutes to 48 hours, and more preferably for 30 minutes to 24 hours. More preferably, the organic solvent is selected from the group consisting of THF, ethyl ether and toluene.

In a preferred embodiment of the invention, step b) further comprises:

i) deprotecting the compound of formula (IV) at the presence of an acid to obtain a compound of formula (Ia),

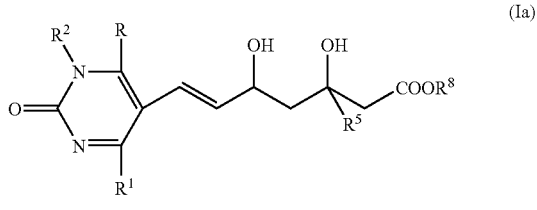

(Ia)

in which R, $R^1$, $R^2$, $R^5$ and $R^8$ are as defined previously; and ii) if desired, converting the compound of formula (Ia) into other compounds of formula (I).

As would be understood by those skilled in the art, the compound of formula (Ia) is actually a compound of formula (I), where Y is

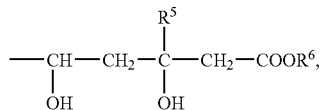

and $R^6$ is alkyl or aryl.

The acid used in step i) may be various conventional inorganic or organic acids, such as hydrochloric acid, sulfuric acid, acetic acid, and the like. Preferably, step i) is carried out in an organic solvent, at a temperature ranging from −20° C. to the reflux temperature of the solvent, for 30 minutes to 15 hours. More preferably, the organic solvent used is a polar solvent, including, but not limited to, alcohols, ethers and the like, and even more preferably the solvent is selected from the group consisting of methanol, ethanol, DMF, THF, DMSO, and a mixed solvent of methanol and THF.

The expression "if desired" as recited in step ii) refers to the circumstance that the desired compound of formula (I) is different from the compound of formula (Ia). As would be understood by those skilled in the art, step ii) may be carried out according to various conventional methods well-known in the art.

For example, in the cases where B is —CH═CH—:

a compound of formula (I), where $R^6$ is hydrogen, can be prepared from the compound of formula (Ia) by hydrolysis under acidic condition, or by hydrolysis under basic condition followed by acidification;

a compound of formula (I), where $R^6$ is a pharmacologically non-toxic ion (such as $Na^+$, $K^+$, $Ca^{2+}$ and $NH_4^+$), can be prepared by reacting the compound of formula (Ia) or the compound of formula (I), where $R^6$ is hydrogen, with a corresponding base (such as NaOH, KOH, $CaOH_2$ and $NH_4OH$), or be prepared from a compound of formula (I), where $R^6$ is a different cation, by a cation-exchange reaction, such as a reaction of a compound, where $R^6$ is $Na^+$, and $CaCl_2$ so as to replace the $Na^+$ ion with $Ca^{2+}$ ion;

other compounds of formula (I), where $R^6$ represents alkyl, alkenyl, aryl, aralkyl or alkaryl, can be prepared by esterification of a compound of formula (I), where $R^6$ is hydrogen, with a corresponding alcohol; and a compound of formula (I), where Y is a lactone, can be prepared by heating a solution of a compound of formula (Ia) to reflux.

Meanwhile, a compound of formula (I), where B is —$CH_2$—$CH_2$—, can be prepared from a compound of formula (I), where B is —CH═CH—, by catalyzed hydrogenation.

Still another aspect of the invention is directed to an intermediate of formula (II),

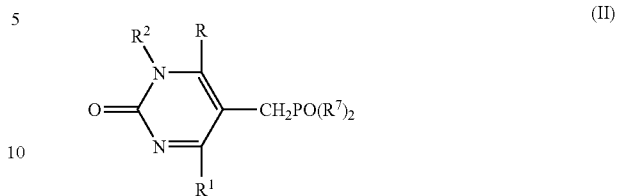

(II)

in which R, $R^1$, $R^2$ and $R^7$ are as defined previously.

In preferred embodiments of the invention, the compound of formula (II) can be prepared by the following steps:

1) reacting a compound of formula (V),

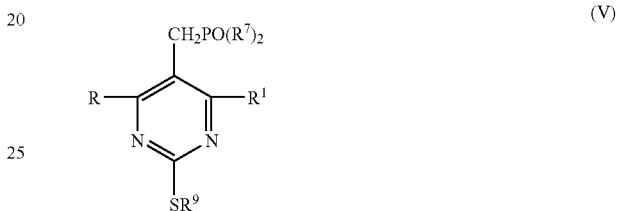

(V)

in which R, $R^1$ and $R^7$ are as defined previously, and $R^9$ is alkyl or aryl, at the presence of a base or an acid, so as to obtain a compound of formula (IIa),

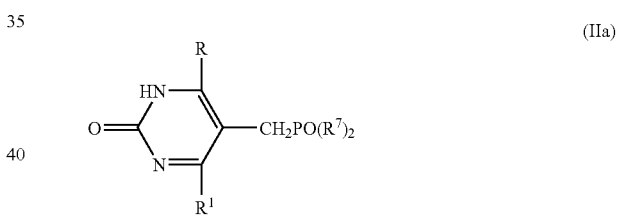

(IIa)

in which R, $R^1$ and $R^7$ are as defined previously; and 2) if desired, reacting the compound of formula (IIa) with a compound of formula (VI),

$R^2$—Z (VI)

in which $R^2$ is as defined previously but not hydrogen, and Z is halogen, at the presence of a base, so as to obtain the compound of formula (II).

As would be understood by those skilled in the art, the compound of formula (IIa) is actually a compound of formula (II), where $R^2$ is hydrogen.

The base may be used in step 1) includes oxides, hydroxides, carbonates and acetates of alkali metals and alkaline-earth metals, and the like, such as KOH, NaOH, $Na_2CO_3$ and NaOAc. Suitable acids include various inorganic acids, lower organic acids, and the like, such as HCl, $H_2SO_4$, $HCO_2H$ and AcOH etc.

Solvents may be used in step 1) include organic polar solvents and water. More preferably, the solvent used is methanol and/or water. The reaction of step 1) is carried out at a temperature ranging from −40° C. to the reflux temperature of the solvent, more preferably at room temperature.

Preferably, the base used in step 2) is selected from the group consisting of metal oxides, alkyl lithium, carbonates, acetates, organic amino lithium, organic amines, and oxides and hydroxides of alkali metasl and alkaline-earth metals, including, but not limited to, NaH, LiH, CaH$_2$, LiBu-n, LiCl, Li$_2$CO$_3$, Na$_2$CO$_3$, NaOAc, NaOH, KOH and triethylamine. More preferably, the base is selected from the group consisting of NaH, KOH and NaOH.

Solvents may be used in step 2) include organic solvents and water. More preferably, the solvent used is an organic polar solvent, such as DMF, DMSO, methanol, and water. The reaction of step 2) is carried out at a temperature ranging from −40° C. to the reflux temperature of the solvent, more preferably at room temperature.

Alternatively, the compound of formula (IIa) can be prepared by reacting a cmpound of formula (Va),

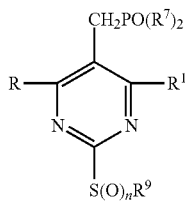

(Va)

in which R, R$^1$, R$^7$ and R$^9$ are as defined previously, and n is 1 or 2, at the presence of an acid or a base.

The compound of formula (Va) can be prepared from the compound of formula (V) by oxidation, in which suitable oxidants include inorganic oxides and organic peroxides, preferably inorganic and organic peroxides, such as H$_2$O$_2$, peroxyacetic acid, and metachloroperbenzoic acid (m-CPBA) etc. The reaction may be carried out in an organic solvent, such as CH$_2$Cl$_2$, CHCl$_3$ and toluene etc. Preferably, the reaction is carried out at a temperature ranging form −40° C. to the reflux temperature of the solvent, more preferably at room temperature.

In a further preferred embodiment of the invention, the compound of formula (V) can be prepared by reacting a compound of formula (VII),

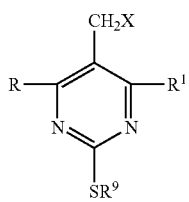

(VII)

in which R, R$^1$ and R$^9$ are as defined previously, and X is halogen, with an organic phosphorous compound of formula (VIII),

POR$^{10}$(R$^7$)$_2$ (VIII)

in which R$^7$ is as defined previously, and R$^{10}$ is alkyl or aryl.

Preferred organic phosphorous compounds include P(OCH$_3$)$_3$, P(OEt)$_3$, P(OCH$_3$)Ph$_2$ and P(OEt)Ph$_2$.

The compound of formula (VII) can be prepared from a compound of formula (X) by reduction followed by halogenation,

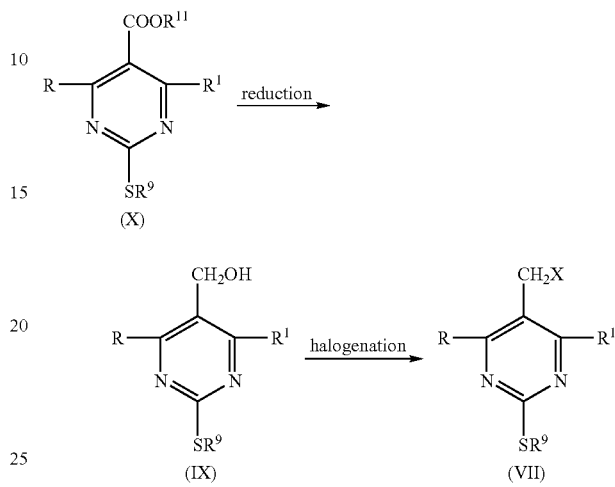

in which R, R$^1$, R$^9$ and X are as defined previously, and R$^{11}$ is alkyl.

According to some preferred embodiments of the invention, the compound of formula (X) can be prepared according to the method as described in U.S. Pat. No. 5,260,440.

The above-mentioned reduction can be preformed by catalyzed hydrogenation with, for example, H$_2$/Pt, H$_2$/PtO$_2$, H$_2$/Pt(OH)$_2$, H$_2$/Pd or H$_2$/PdO$_2$, or with hydrogenating agents containing boron or aluminum, such as KBH$_4$, NaBH$_4$, LiAlH$_4$ and AlHR$_2$ etc. More preferably, the hydrogenating agents of LiAlH$_4$ and diisobutyl aluminum hydride (DBAI-H) can be used.

The reduction is preferably carried out at the presence of an anhydrous inert organic solvent, including ethyl ether, tetrahydrofuran, toluene and benzene etc., and more preferably ethyl ether and toluene. Preferably, the reduction is carried out at a temperature ranging from −78° C. to the reflux temperature of the solvent, more preferably from 0° C. to room temperature.

Halogenating agents may be used in the halogenation process include, but are not limited to, X$_2$, COX$_2$, (COX)$_2$, SOX$_2$, SO$_2$X$_2$, PX$_3$ and POX$_3$ etc., where X represents a halogen. More preferably, the halogenating agent is selected from the group consisting of COCl$_2$, SOCl$_2$, PBr$_3$ and POCl$_3$.

EXAMPLES

Hereinafter, the invention will be illustrated more in detail by the following examples, which, however, should be considered to be non-limiting and only illustrative of some preferred embodiments of the present invention.

The chemical structures of some compounds as well as the reaction scheme involved in the examples are as shown below:

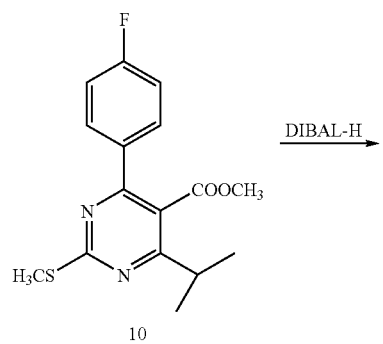
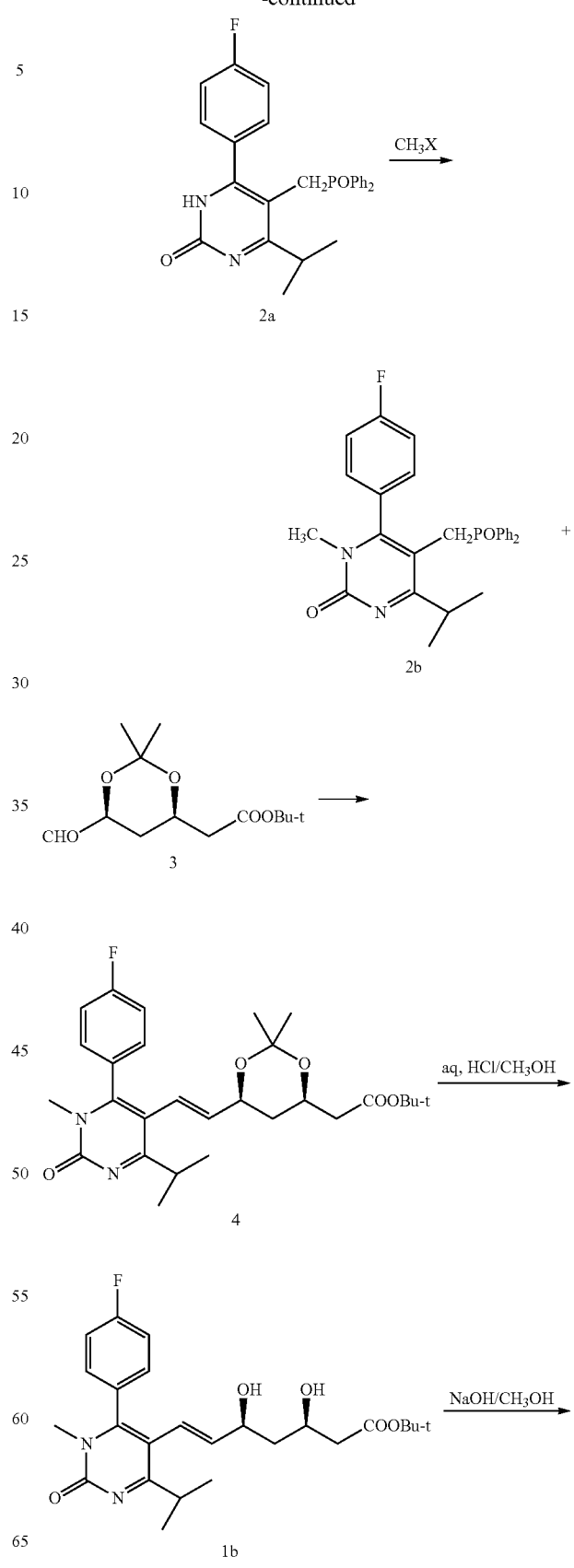

-continued

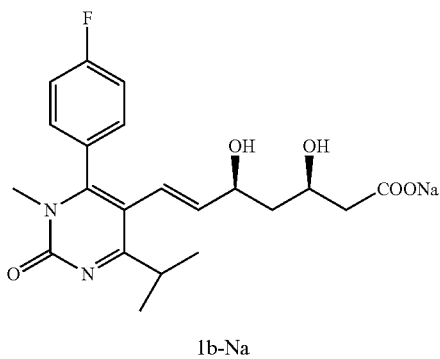

1b-Na

Preparation 1

Preparation of 4-(4'-fluorophenyl)-6-isopropyl-2-methylthio-5-hydroxymethyl-pyrimidine (9)

20 g (62.5 mmol) of methyl 4-(4'-fluorophenyl)-6-isopropyl-2-methylthio-pyrimidin-5-yl-carboxylate (10) and 300 mL of dry anhydrous toluene were loaded in a IL three-neck round bottomed flask, equipped with a mechanical stirrer and an air duct, and stirred under a nitrogen atmosphere. 100 mmol of diisobutyl aluminum hydride (DIBAl-H) was then added in batches into the mixture while cooling in an ice-salt bath. After TLC assay showed that the starting compound (10) was depleted, the reaction mixture was warmed up to room temperature and further reacted for 2-3 hours. 500 mL of water was then added, and the organic layer was collected, washed with water (200 mL×2) and a saturated solution of sodium chloride (200 mL×1), and then dried overnight over anhydrous magnesium sulfate. The mixture was then filtered, evaporated under reduced pressure to remove the solvent, and recrystallized in ethyl acetate, obtaining 16 g of a white crystal, yield 88%.

M.P(° C.): 140-142.

EI-MS (m/z): 292(M+).

Preparation 2

Preparation of 4-(4'-fluorophenyl)-6-isopropyl-2-methylthio-5-bromomethyl-pyrimidine (7)

14.6 g (50 mmol) of compound (9) and 200 ml of dichloromethane were added into a 500 mL three-neck round bottomed flask, equipped with a mechanical stirrer and a dropping funnel, followed by addition of 67 g (0.1 mol) of phosphorus tribromide dropwise at room temperature. After TLC assay showed that the starting compound (9) was depleted, 100 mL of water was added, and the organic layer was collected. The organic phase was then washed with 5% aqueous NaHCO$_3$ solution, dried over anhydrous calcium chloride, and evaporated under reduced pressure to remove the solvent, obtaining 16 g raw product of compound (7), which was used directly in the next step without purification.

EI-MS (m/z): 354(M+).

Preparation 3

Preparation of [4-(4'-fluorophenyl)-6-isopropyl-2-methylthio-pyrimidin-5-yl]-methyl diphenyl phosphonate (5)

14.2 g (40 mmol) of compound (7), 13.8 g of ethoxyl diphenyl phosphine and 200 ml of toluene were added into a 500 mL three-neck round bottomed flask, equipped with a mechanical stirrer and a reflux condensing tube, and refluxed for 10 hours. The mixture was then evaporated under reduced pressure to remove the solvent, and recrystallized in ethyl acetate, obtaining 17.1 g of a white crystal, yield 90%.

EI-MS (m/z): 476(M+).

Preparation 4

Preparation of [4-(4'-fluorophenyl)-6-isopropyl-2-mesyl-pyrimidin-5-yl]-methyl diphenyl phosphonate (5a)

7.5 g (15.6 mmol) of compound (5), and 100 ml of chloroform were stirred in a 250 mL three-neck flask equipped with a mechanical stirrer, followed by addition of 5.4 g (39.1 mmol) of metachloroperbenzoic acid, and then reacted for 2 hours at room temperature. After TLC assay showed that the starting compound (5) was depleted, the reaction mixture was transferred to a 350 mL tap funnel, and the organic layer was collected. The organic phase was then washed in turn by aqueous K$_2$SO$_4$ solution, saturated aqueous NaHCO$_3$ solution, and saturated aqueous NaCl solution, dried overnight over anhydrous magnesium sulfate, filtered, and evaporated under reduced pressure to remove the solvent, obtaining a white solid product. The solid was recrystallized in acetone/petroleum ether to afford 7.21 g of compound (5a) as a white needle crystal, yield 91%.

EI-MS (m/z): 508(M+).

Preparation 5

Preparation of [4-(4'-fluorophenyl)-6-isopropyl-2-oxo-pyrimidin-5-yl]-methyl diphenyl phosphonate (2a)

7.6 g (15 mmol) of compound (5a), and 60 mL (30 mmol) of 0.5N aqueous NaOH solution were added in a 250 mL three-neck flask equipped with a mechanical stirrer. After reaction at room temperature for 0.5 hr, the mixture was heated to 60° C. for another 0.5 hr, with the TLC assay showing that the starting compound (5a) was depleted. The reaction mixture was neutralized to pH 6-7 with a 1N aqueous HCl solution, obtaining a brown-yellow dope, which was then recrystallized in methanol/ethanol to afford 5.42 g of compound (2a) as a light yellow solid, yield 81%.

EI-MS (m/z): 446(M+).

Preparation 6

Preparation of [4-(4'-fluorophenyl)-6-isopropyl-2-oxo-3-methyl-pyrimidin-5-yl]-methyl diphenyl phosphonate (2b)

11.15 g (25 mmol) of compound (2a), 100 mL DMF and 1.2 g (30 mmol) NaOH were added in a 500 mL three-neck round bottomed flask, equipped with a mechanical stirrer and a constant pressure dropping funnel. 33 mmol of iodomethane was then added slowly dropwise under stirring, and further stirred for 2 hours after the addition. The reaction mixture was poured into 200 mL water, and extracted with ethyl acetate. The organic phase was combined, dried over $CaCl_2$, and evaporated under reduced pressure to remove the solvent. The residue was purified by chromatography on silica gel column with petroleum ether/ethyl acetate as an eluant to afford 5.6 g of compound (2b).

EI-MS (m/z): 460(M+).

Preparation 7

Preparation of Tertbutyl 7-[4'-(4"-fluorophenyl)-6'-isopropyl-2'-oxo-3'-methyl-pyrimidin-5'-yl]-(3R,5S, 6E)-3,5-isopropylidenedioxo-heptenoate (4)

4.6 g (10 mmol) of compound (2b) and 50 mL of dry DMF were added in a 100 mL three-neck round bottomed flask, equipped with a mechanical stirrer, a constant pressure dropping funnel and an air duct. The mixture was then cooled to −78° C., and 10 mL (10 mmol) of 1M tert-butyl lithium in n-hexane was added slowly dropwise under nitrogen atmosphere, and reacted for 30 minutes. 2.85 g (11 mmol) of compound (3) in 20 mL THF was then added slowly dropwise, and the reaction mixture was warmed up slowly to 0° C. for 3 hours, and further warmed up to room temperature for 2 hours. After addition of 100 mL water and 200 mL dichloromethane, the organic layer was separated, dried over anhydrous magnesium sulfate, evaporated under reduced pressure to remove the solvent, and purified by chromatography on silica gel column, obtaining 3.17 g of (E)-compound (4) as an oil, yield 63%.

FAB(m/z): 501(M+).

Example 1

Tert-butyl (E)-7-[4'-(4"-fluorophenyl)-6'-isopropyl-2'-oxo-3'-methyl-pyrimidin-5'-yl]-(3R,5S)dihydroxyl-hept-6-enoate (1b)

2.17 g of compound (4), 10 mL of 60% acetic acid solution, 0.5 mL of 1N HCL and 50 mL methanol were added in a 100 mL reaction flask, heated to 50° C., and reacted for 3 hours under stirring. The mixture was then cooled to room temperature, poured into 100 mL water, and extracted with ethyl acetate (3×50 mL). The organic phase was combined, washed in turn with 5% $Na_2CO_3$ solution, water and saturated aqueous solution of sodium chloride, dried over anhydrous magnesium sulfate, and evaporated under reduced pressure to remove the solvent. The residue was purified by chromatography on silica gel column to afford 1.67 g of compound (1b) as an oil, yield 83%.

FAB(m/z): 460(M+).

Example 2

Sodium (E)-7-[4'-(4"-fluorophenyl)-6'-isopropyl-2'-oxo-3'-methyl-pyrimidin-5'-yl]-(3R,5S)dihydroxyl-hept-6-enoate (1b-Na)

1.6 g (3.5 mmol) of compound (1b) was dissolved in 100 mL methanol, and then 38 mL of 0.1N aqueous NaOH solution was added dropwise while cooling in ice-water. The mixture was then warmed up to room temperature and reacted for 2 hours. After removing the solvent under reduced pressure, the residue was ground with ethyl ether to afford 1.38 g product as a light yellow solid, yield 92%.

M.P(° C.): 145.

$[\alpha]_{20/D}$+11.67° (c 0.18 $CH_3OH$).

FAB(m/z): 405(M+1).

$^1$H-NMR (DMSO-$d_6$) δ (ppm): 0.583-0.892 (m, 1H), 1.130-1.144 (6, 6H), 1.202-1.262 (m, 1H), 1.694-1.733 (dd, 1H), 1.912-1.943 (dd, 1H), 3.073 (s, 3H), 3.140-1.184 (m, 1H), 3.369-3.397 (m, 1H), 3.587-3.598 (d, 1H), 3.975 (m, 1H), 4.855 (m, 1H), 5.206-5.242 (dd, 1H), 5.957-5.983 (d, 1H), 7.305-7.335 (m, 2H), 7.422-7.482 (m, 2H).

The compounds of Examples 3-9 were prepared according to reaction schemes and processes substantially the same as those described in Preparation Examples 1-7 and Examples 1-2, under similar conditions.

Example 3

Sodium (E)-7-[4'-(4"-fluorophenyl)-6'-isopropyl-2'-oxo-pyrimidin-5'-yl]-(3R,5S) dihydroxyl-hept-6-enoate (1a-Na)

M.P(° C.): >260.

$[\alpha]_{20/D}$−3.12° (c 0.16 $CH_3OH$).

FAB(m/z): 391(M+1).

$^1$H-NMR (DMSO-$d_6$) δ (ppm): 1.062-1.085 (t, 2H), 1.117-1.128 (d, 6H), 1.160-1.200 (m, 1H), 1.411-1.459 (m, 1H), 1.855-1.895 (dd, 1H), 2.045-2.077 (dd, 1H), 3.161-3.205 (m, 1H), 3.439-3.474 (dd, 1H), 3.610-3.637 (m, 1H), 4.038-4.071 (dd, 1H), 5.086-5.123 (dd, 1H), 6.246-6.272 (d, 1H), 7.131-7.160 (m, 2H), 7.447-7.471 (m, 2H).

Example 4

Sodium (E)-7-[4'-(4"-methylphenyl)-6'-isopropyl-2'-oxo-3'-benzyl-pyrimidin-5'-yl]-(3R,5S)dihydroxyl-hept-6-enoate (1c-Na)

M.P(° C.): 156.

$[\alpha]_{20/D}$+6.7° (c 0.28 $CH_3OH$).

ESI-MS (m/z): 479(M+1).

$^1$H-NMR (DMSO-$d_6$) δ (ppm): 0.825-0.851 (m, 1H), 1.163-1.174 (d, 6H), 1.205-1.237 (m, 1H), 1.686-1.715 (dd, 1H), 1.881-1.931 (dd, 1H), 3.162-3.206 (m, 1H), 3.650-3.670, 3.373-3.386 (m, 1H), 3.953-3.957 (d, 1H), 4.886 (s, 2H), 5.231-5.266 (dd, 1H), 5.955-5.961 (d, 1H), 6.835-7.300 (m, 9H).

Example 5

Sodium (E)-7-[4'-(4"-fluorophenyl)-6'-isopropyl-2'-oxo-3'-(benzyloxymethyl)-pyrimidin-5'-yl]-(3R,5S) dihydroxyl-hept-6-enoate (1d-Na)

M.P(° C.): 134.

$[\alpha]_{20/D}$−61.67° (c 0.12 $CH_3OH$).

ESI-MS (m/z): 509(M+1).

$^1$H-NMR (DMSO-$d_6$) δ (ppm): 0.816-0.854 (m, 1H), 1.165-1.174 (d, 6H), 1.196-1.233 (m, 1H), 1.676-1.715 (dd, 1H), 1.891-1.921 (dd, 1H), 3.172-3.216 (m, 1H), 3.375-3.389 (m, 1H), 3.957-3.967 (d, 1H), 4.896 (s, 2H), 5.241-5.276 (dd, 1H), 5.945-5.971 (d, 1H), 6.858-7.316 (m, 9H).

Example 6

Tert-butyl (E)-7-[4'-(4"-fluorophenyl)-6'-isopropyl-2'-oxo-3'-(ethoxylmethyl)-pyrimidin-5'-yl]-(3R,5S) dihydroxyl-hept-6-enoate (1e)

A colorless oil.
ESI-MS (m/z): 505(M+1).

Example 7

Tert-butyl (E)-7-[4'-(4"-fluorophenyl)-6'-isopropyl-2'-oxo-3'-(2"-ethoxylethyl)-pyrimidin-5'-yl]-(3R,5S) dihydroxyl-hept-6-enoate (1f)

A colorless oil.
ESI-MS (m/z): 519(M+1).

Example 8

Tert-butyl (E)-7-[4'-(4"-fluorophenyl)-6'-isopropyl-2'-oxo-3'-cyclopropyl-pyrimidin-5'-yl]-(3R,5S)dihydroxyl-hept-6-enoate (1g)

A colorless oil.
ESI-MS (m/z): 487(M+1).

Example 9

Tert-butyl (E)-7-[4'-(4"-fluorophenyl)-6'-isopropyl-2'-oxo-3'-cyclopropylmethyl-pyrimidin-5'-yl]-(3R,5S)dihydroxyl-hept-6-enoate (1h)

A colorless oil.
ESI-MS (m/z): 501(M+1).

Biological Activity Experiments

1. Preparation of Homogenate of Rat Liver Cells

Healthy pure line SPF SD male rats having a body weight of 200-250 g were used in the experiment. After being fed regularly with ordinary diets, the rats were decapitated for bloodletting, and their livers were removed, washed to remove residual blood, and homogenized with a phosphate buffered solution (PBS) in a homogenizer. The resulting homogenate was then filtered through a double-layer gauze. The concentration of proteins in the homogenate was measured using Bradford method and adjusted to 500 μg/μL.

2. Measurement of the HMG-CoA Reductase Inhibitory Effect

The light adsorption of NADPH, which indicates the activity and reaction rate of HMG-CoA reductase, was measured by spectrophotometry at the wavelength of 339 nm. A 0.5 mL system containing 70 mmol/L phosphate buffer (pH 6.5), 2 mmol/L EDTA, 2 mmol/L cysteamine, 0.06% BSA, 0.25 mmol/L NADPH and 100 μL liver homogenate was used for testing the enzyme activity. 50 μL of a test compound was added to the testing system and homogenized, and a substrate of HMG-CoA was then added till a concentration of 50 μmol/L to initiate the reaction. Then the obtained solution was kept in a water bath of 25° C. for 5 minutes before addition to a cuvette. Liver homogenate preserved in a refrigerator was pre-activated in a water bath of 37° C., and then added to the testing solution. Kept at the temperature of 25° C., the absorption of the solution was measured every 30 seconds at 339 nm within 840 seconds. The maximal adsorption was observed at second 0, and the reduction ratio of the adsorption at a specific time to that at second 0 indicates the extent of the inhibition of the activity of HMG-CoA reductase by the test compound. A smaller reduction ratio (absolute value) indicates a higher inhibition on the activity of the HMG-CoA reductase by the test compound.

Relative activity of HMG-CoA reductase=(Ao−An)/Ao×100% where: An: Absorption (λ=339 nm) at second n;
Ao: Absorption (λ=339 nm) at second 0.

FIG. 1 shows the relative activity (%) of HMG-CoA reductase for each test compound at a concentration of 100 mg/L at various time points.

The results as shown in FIG. 1 indicate that the compound of the invention has a potent inhibitory effect on HMG-CoA reductase, and is superior to sodium lovastatin.

The invention claimed is:

1. A compound of formula (I),

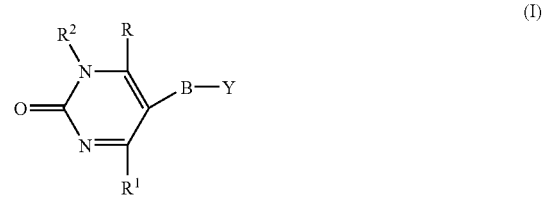

wherein

R and $R^1$ are independently selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $R^3R^4N$—, $NO_2$, CN, OH, $C_1$-$C_6$ alkyl, $C_1$-$C_6$ haloalkyl, $C_1$-$C_6$ alkoxy, $C_6$-$C_{12}$ aryloxy, $C_7$-$C_{20}$ aralkoxy, $C_1$-$C_6$ alkanoyl, sulfonyl and sulfinyl, where each $R^3$ and $R^4$ independently represents H, $C_1$-$C_6$ alkyl or $C_6$-$C_{12}$ aryl;

$R^2$ is selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $R^3R^4N$—, $NO_2$, CN, OH, $C_1$-$C_6$ alkyl, $C_3$-$C_8$ cycloalkyl, $C_6$-$C_{12}$ aryl, $C_1$-$C_6$ alkoxy, $C_6$-$C_{12}$ aryloxy, $C_7$-$C_{20}$ aralkoxy, $C_1$-$C_6$ alkylthio, $C_6$-$C_{12}$ arylthio, $C_7$-$C_{20}$ aralkylthio, $C_1$-$C_6$ alkanoyl, sulfonyl and sulfinyl, where $R^3$ and $R^4$ are as defined previously;

B is —$CH_2$—$CH_2$— or —CH=CH—; and
Y represents

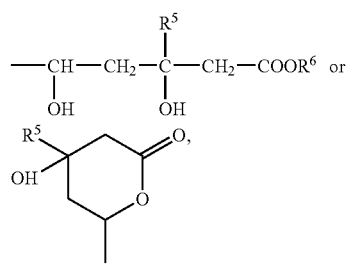

wherein R⁵ is hydrogen or $C_1$-$C_6$ alkyl, and R⁶ represents hydrogen, $C_1$-$C_6$ alkyl, $C_2$-$C_6$ alkenyl, $C_6$-$C_{12}$ aryl, $C_7$-$C_{20}$ aralkyl, $C_7$-$C_{20}$ alkaryl or a pharmacologically non-toxic ion.

2. The compound according to claim 1, wherein R and R¹ are independently selected from the group consisting of hydrogen, $C_1$-$C_6$ alkyl and $C_6$-$C_{12}$ aryl groups, which (except hydrogen) may be substituted by 1 to 3 substituents selected from the group consisting of F, Cl, $NO_2$, CN, OH, $C_1$-$C_6$ alkyl, $C_1$-$C_6$ haloalkyl, and $C_1$-$C_6$ alkoxy.

3. The compound according to claim 1, wherein R² is selected from the group consisting of hydrogen, $C_1$-$C_6$ alkyl, $C_3$-$C_8$ cycloalkyl and $C_6$-$C_{12}$ aryl groups, which (except hydrogen) may be substituted by 1 to 3 substituents selected from the group consisting of F, Cl, $NO_2$, CN, OH, $C_1$-$C_6$ alkyl, $C_3$-$C_8$ cycloalkyl, $C_6$-$C_{12}$ aryl, $C_1$-$C_6$ alkoxy, $C_6$-$C_{12}$ aryloxy, $C_1$-$C_6$ alkylthio and $C_6$-$C_{12}$ arylthio.

4. The compound according to claim 1, wherein R⁶ represents hydrogen, $C_1$-$C_6$ alkyl, $C_6$-$C_{12}$ aryl, or $Na^+$, $K^+$ or $Ca^{2+}$ ions.

5. The compound according to claim 1, wherein B is (E)-CH=CH—.

6. The compound according to claim 1, wherein the hydroxyl group at the 3 position and the hydroxyl group at the 5 position of the Y chain are present in a (3R,5S) configuration.

7. The compound according to claim 1, wherein

R and R¹ are independently selected from the group consisting of $C_1$-$C_6$ alkyl, and $C_6$-$C_{12}$ aryl groups, which may be substituted by 1 to 3 substituents selected from the group consisting of F, Cl, $NO_2$, CN and $C_1$-$C_6$ alkyl;

R² is selected from the group consisting of hydrogen, $C_1$-$C_6$ alkyl, $C_3$-$C_6$ cycloalkyl, and $C_6$-$C_{12}$ aryl groups, which (except hydrogen) may be substituted by 1 to 3 substituents selected from the group consisting of OH, $C_1$-$C_6$ alkyl, $C_3$-$C_6$ cycloalkyl, $C_6$-$C_{12}$ aryl, $C_1$-$C_6$ alkoxy and $C_6$-$C_{12}$ aryloxy;

R⁵ is hydrogen or $C_1$-$C_6$ alkyl; and

R⁶ represents hydrogen, $C_1$-$C_6$ alkyl, or $Na^+$, $K^+$, or $Ca^{2+}$ ions.

8. The compound according to claim 7, which is selected from tert-butyl (E)-7-[4'-(4''-fluorophenyl)-6'-isopropyl-2'-oxo-3'-methyl-pyrimidin-5'-yl]-(3R,5S)dihydroxyl-hept-6-enoate;

sodium (E)-7-[4'-(4''-fluorophenyl)-6'-isopropyl-2'-oxo-3'-methyl-pyrimidin-5'-yl]-(3R,5S)dihydroxyl-hept-6-enoate;

sodium (E)-7-[4'-(4''-fluorophenyl)-6'-isopropyl-2'-oxo-pyrimidin-5'-yl]-(3R,5S) dihydroxyl-hept-6-enoate;

sodium (E)-7-[4'-(4''-methylphenyl)-6'-isopropyl-2'-oxo-3'-benzyl-pyrimidin-5'-yl]-(3R,5S)dihydroxyl-hept-6-enoate;

sodium (E)-7-[4'-(4''-fluorophenyl)-6'-isopropyl-2'-oxo-3'-(benzyloxymethyl)-pyrimidin-5'-yl]-(3R,5S)dihydroxyl-hept-6-enoate;

tert-butyl (E)-7-[4'-(4''-fluorophenyl)-6'-isopropyl-2'-oxo-3'-(ethoxylmethyl)-pyrimidin-5'-yl]-(3R,5S)dihydroxyl-hept-6-enoate;

tert-butyl (E)-7-[4'-(4''-fluorophenyl)-6'-isopropyl-2'-oxo-3'-(2''-ethoxylethyl)-pyrimidin-5'-yl]-(3R,5S)dihydroxyl-hept-6-enoate;

tert-butyl (E)-7-[4'-(4''-fluorophenyl)-6'-isopropyl-2'-oxo-3'-cyclopropyl-pyrimidin-5'-yl]-(3R,5S)dihydroxyl-hept-6-enoate; and tert-butyl (E)-7-[4'-(4''-fluorophenyl)-6'-isopropyl-2'-oxo-3'-cyclopropylmethyl-pyrimidin-5'-yl]-(3R,5S)dihydroxyl-hept-6-enoate.

9. A pharmaceutical composition, comprising an effective amount of the compound of any one of claims 1-8, and a pharmaceutically acceptable carrier.

10. A method for treating diabetes mellitus, in a subject, comprising administering to the subject an effective amount of the compound of any one of claims 1-8.

11. The method according to claim 10, wherein the treatment is associated with inhibition of HMG-CoA reductase.

12. A process for the preparation of a compound of formula (I),

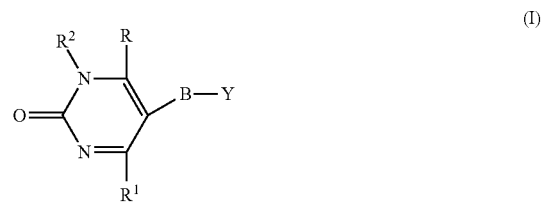

wherein

R and R¹ are independently selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $R^3R^4N$—, $NO_2$, CN, OH, $C_1$-$C_6$ alkyl, $C_1$-$C_6$ haloalkyl, $C_1$-$C_6$ alkoxy, $C_6$-$C_{12}$ aryloxy, $C_7$-$C_{20}$ aralkoxy, $C_1$-$C_6$ alkanoyl, sulfonyl and sulfinyl, where each R³ and R⁴ independently represents H, $C_1$-$C_6$ alkyl or $C_6$-$C_{12}$ aryl;

R² is selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $R^3R^4N$—, $NO_2$, CN, OH, $C_1$-$C_6$ alkyl, $C_3$-$C_8$ cycloalkyl, $C_6$-$C_{12}$ aryl, $C_1$-$C_6$ alkoxy, $C_6$-$C_{12}$ aryloxy, $C_7$-$C_{20}$ aralkoxy, $C_1$-$C_6$ alkylthio, $C_6$-$C_{12}$ arylthio, $C_7$-$C_{20}$ aralkylthio, $C_1$-$C_6$ alkanoyl, sulfonyl and sulfinyl, where R³ and R⁴ are as defined previously;

B is —$CH_2$—$CH_2$— or —CH=CH—; and

Y represents

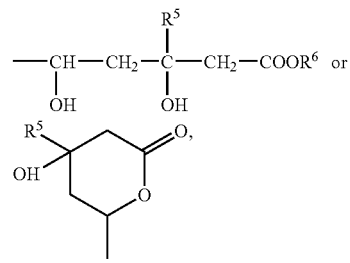

wherein R⁵ is hydrogen or $C_1$-$C_6$ alkyl, and R⁶ represents hydrogen, $C_1$-$C_6$ alkyl, $C_2$-$C_6$ alkenyl, $C_6$-$C_{12}$ aryl, $C_7$-$C_{20}$ aralkyl, $C_7$-$C_{20}$ alkaryl or a pharmacologically non-toxic ion, which comprises:

a) reacting a compound of formula (II),

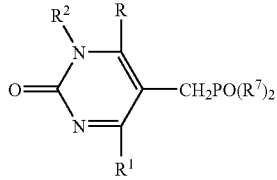
(II)

wherein R, $R^1$ and $R^2$ are as defined previously, and $R^7$ represents $C_1$-$C_6$ alkyl, $C_1$-$C_6$ alkoxy, $C_6$-$C_{12}$ aryl or $R^3R^4N$—, where $R^3$ and $R^4$ are as defined previously, with a compound of formula (III),

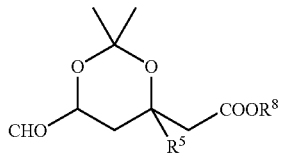
(III)

wherein $R^5$ is as defined previously and $R^8$ is $C_1$-$C_6$ alkyl or $C_6$-$C_{12}$ aryl, so as to obtain a compound of formula (IV),

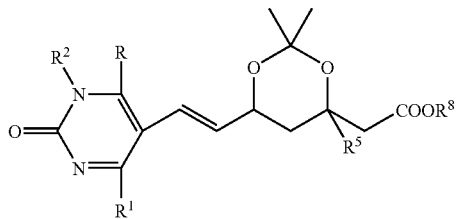
(IV)

wherein R, $R^1$, $R^2$, $R^5$ and $R^8$ are as defined previously; and b) converting the compound of formula (IV) into the compound of formula (I).

13. The process according to claim 12, wherein step b) further comprises:

i) deprotecting the compound of formula (IV) at the presence of an acid to obtain a compound of formula (Ia),

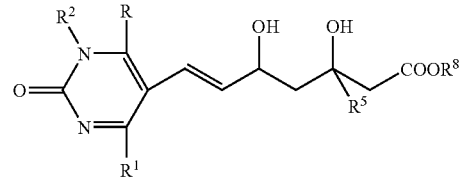
(Ia)

wherein R, $R^1$, $R^2$, $R^5$ and $R^8$ are as defined previously; and ii) if desired, converting the compound of formula (Ia) into the compound of formula (I).

14. A compound of formula (II),

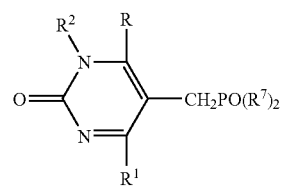
(II)

wherein

R and $R^1$ are independently selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $R^3R^4N$—, $NO_2$, CN, OH, $C_1$-$C_6$ alkyl, $C_1$-$C_6$ haloalkyl, $C_1$-$C_6$ alkoxy, $C_6$-$C_{12}$ aryloxy, $C_7$-$C_{20}$ aralkoxy, $C_1$-$C_6$ alkanoyl, sulfonyl and sulfinyl, where each $R^3$ and $R^4$ independently represents H, $C_1$-$C_6$ alkyl or $C_6$-$C_{12}$ aryl;

$R^2$ is selected from the group consisting of hydrogen, $C_1$-$C_6$ alkyl, $C_3$-$C_8$ cycloalkyl, $C_2$-$C_6$ alkenyl, $C_3$-$C_8$ cycloalkenyl, $C_6$-$C_{12}$ aryl and $C_5$-$C_{11}$ heteroaryl groups, which (except hydrogen) may be substituted by 1 to 3 substituents selected from the group consisting of halogen, $R^3R^4N$—, $NO_2$, CN, OH, $C_1$-$C_6$ alkyl, $C_3$-$C_8$ cycloalkyl, $C_6$-$C_{12}$ aryl, $C_1$-$C_6$ alkoxy, $C_6$-$C_{12}$ aryloxy, $C_7$-$C_{20}$ aralkoxy, $C_1$-$C_6$ alkylthio, $C_6$-$C_{12}$ arylthio, $C_7$-$C_{20}$ aralkylthio, $C_1$-$C_6$ alkanoyl, sulfonyl and sulfinyl, where $R^3$ and $R^4$ are as defined previously; and $R^7$ represents $C_1$-$C_6$ alkyl, $C_1$-$C_6$ alkoxy, $C_6$-$C_{12}$ aryl or $R^3R^4N$—, where $R^3$ and $R^4$ are as defined previously.

* * * * *